United States Patent [19]

Carnefix

[11] Plant 5,086

[45] Aug. 16, 1983

[54] APPLE TREE

[76] Inventor: Francis W. Carnefix, Box 332, Fruitland, Id. 83619

[21] Appl. No.: 371,651

[22] Filed: Apr. 26, 1982

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—Eugene D. Farley

[57] ABSTRACT

The subject apple tree variety comprises a new Jonathan apple tree (Super Jon) originating as a sport limb mutation of a Jonathan apple tree variety, specifically Jonnee, U.S. Plant Pat. No. 2,934. The new variety of apple tree is generally similar to its parent with respect to trunk, branches, leaves, flowers and fruit but is uniquely characterized by the significantly earlier coloring and maturing of its fruit.

4 Drawing Figures

BACKGROUND AND GENERAL STATEMENT OF THE INVENTION

The present invention relates to a new and distinct variety of apple tree, specifically to the Super Jon strain of Jonathan apple tree.

I discovered my new variety of apple tree in my cultivated apple orchard located at Fruitland, Id. At the time of my discovery I was growing in my orchard a block of trees of the Jonnee variety of Jonathan apples (U.S. Plant Pat. No. 2,934).

While on a routine inspection of the trees, during the middle part of August, I noticed on one of the Jonnee apple trees a single sport limb bearing apples colored bright red and matured to a hard-ripe eating condition. This limb and its fruit were unique on the parent tree and, indeed, throughout the entire block of Jonnee apple trees since the fruit on all the other limbs of the parent tree and on all of the other trees of the orchard block was either green, or but slightly colored, and by no means fully colored and matured to a hard-ripe eating condition.

The fruit borne by the sport limb in question was colored a bright red and ready for market, even at this critical early data which was from 5 to 10 days earlier than the date of ripening of the fruit borne by the remaining limbs of the parent Jonnee tree, and of the remaining Jonnee trees of the orchard block.

Continued observation of the sport limb mutation over a period of two or three weeks indicated that the condition of the fruit remained stable, although its color gradually darkened to a deeper red.

I subsequently made cuttings from the sport limb in question and reproduced the same by graftings made in my Fruitland, Id. orchard. Continued observation of the original sport limb and the graftings made therefrom confirmed the early maturing and development of fruit color as described above. I have observed that these characteristics persist through the third generation.

THE DRAWINGS

The accompanying drawings illustrate my new Super Jon apple tree and the characteristics of its fruit.

DESCRIPTION OF THE NEW VARIETY

Figure 2:
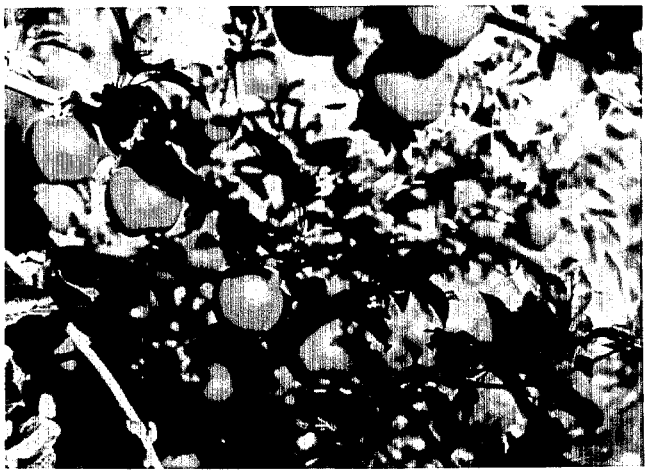
FIG. 2 shows a portion of a typical Super Jon tree of a subsequent generation, with typical leaves and fruit depicted thereon.
Figure 3:
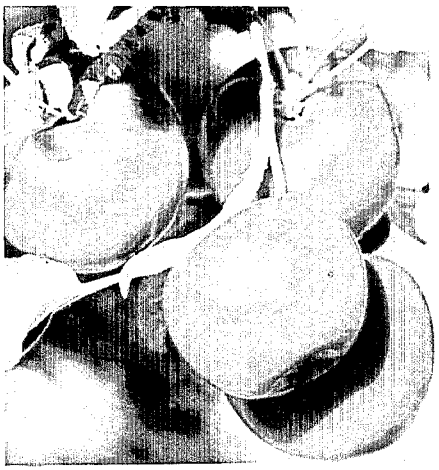
FIG. 3 illustrates the bright red color of my new apple variety in its early stage of maturity.
Figure 1:
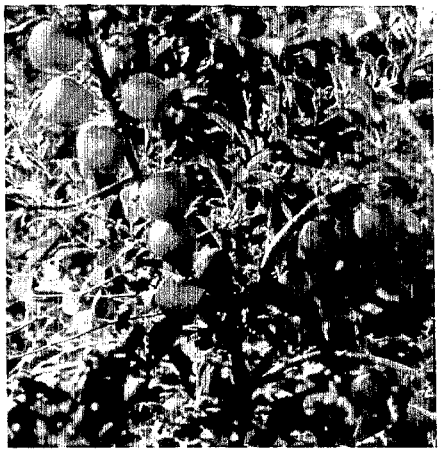
FIG. 1 is a photograph of the parent Jonnee apple tree in its fruit-bearing condition, illustrating the new sport limb mutation of my discovery and the mature and ripened condition of the fruit which it bears, as contrasted with the fruit borne by the other limbs of the tree.
Figure 4:
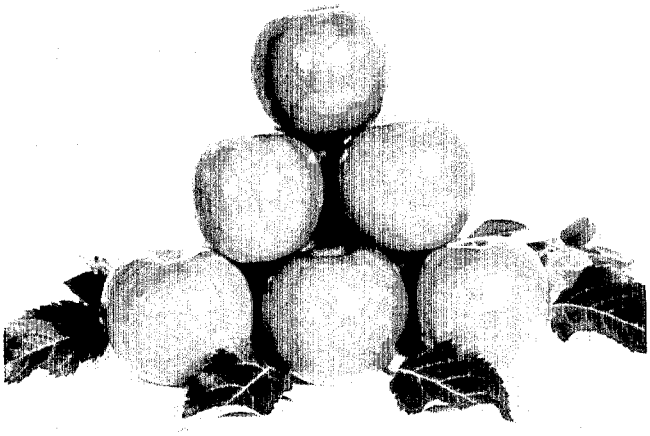
FIG. 4 illustrates the deeper red color of my new apple variety in its later stages of maturity.

A detailed description of my new Super Jon Jonathan apple variety follows, with color terminology being given in accordance with the Standard Color Chart of the Arnold Arboretum, Boston, Mass., except where the color is obvious and described in color terms of ordinary dictionary significance.

Parentage: Sport mutation of Jonee U.S. Plant Pat. No. 2,934.

Locality where grown and observed: Fruitland, Id.

Dates of first and last pickings: August 18 and August 25; Parent variety in the same orchard was first and last picked about August 25 and September 10, respectively.

Tree: Medium size; vigorous; spreading, medium dense, vase formed, rapid grower; hardy, productive, regular bearer.

*Trunk.*—Medium stockiness; medium smoothness.

*Branches.*—Medium thickness, medium smoothness; highly-branched. Color — gray. Lenticels — numerous; medium size.

*Leaves.*—Medium size; oval; abruptly pointed; medium thickness; rugose. Length — from 3 to $3\frac{1}{2}$ inches. Width — from $1\frac{1}{4}$ inches to $1\frac{1}{2}$ inches. Color — dark green. Margin — slightly crenate; dully serrate. Petiole — medium length; medium thickness.

Flowers:

*Dates of first and full bloom.*—About April 25 and May 10, respectively. Size — Medium. Color — White — pink.

Fruit:

*Maturity when described.*—Eating hard ripe; about August 18.

*Size.*—Uniform. Axial diameter — from $2\frac{1}{4}$ inches to $2\frac{3}{4}$ inches. Transverse diameter — from $2\frac{1}{2}$ inches to 3 inches. Transverse to Axial ratio: 0.9.

*Form.*—Uniform; symmetrical, regular; oblate; truncate at base and apex; ovid; slightly ribbed.

*Cavity.*—Symmetrical; acute. Depth — from $\frac{1}{2}$ inch to $\frac{3}{4}$ inch. Breadth — from $\frac{3}{8}$ to $\frac{1}{2}$ inch.

*Basin.*—Symmetrical; abrupt, narrow; 5-crowned, crowns not prominent.

*Stem.*—Clubbed; medium stoutness. Length — about $\frac{3}{4}$ inch or less. Bracts — present; 2 in number.

*Calyx.*—Closed; segments persistent; from acute to acuminate; approximate at base; erect, connivent. Outer surface — pubescent. Inner surface — pubescent.

*Skin.*—Medium thickness; tough, smooth, glossy. Dots — conspicuous; few; large, ruptured; circular; color — whitish cream, distribution — more numerous on apical than basal end. Ground color — yellow. Color markings — faintly striped; bright; color — basically from near bright Moderate Red, Hue 2.5R 4/10 to near bright Strong Red, Hue 5R 4/12. True color typical of variety is achieved 5 to 7 days before parent "Jonee". Some purplish overcast, at maturity but usually darker during earlier stage of immaturity. Bloom — warning. Scarfskin — wanting. General color effect — over-all bright red, with very slight striping apparent.

*Flesh.*—Juicy. Color — white, with yellowish tint. Texture — firm; fine; crisp. Flavor — acid; rich. Aroma — distant. Quality — very high.

*Core.*—Median. Bundle area (longitudinal section) — medium large; ovate; cordate; symmetrical at base; alternate with cell. Halves of area — equal; bundles, inconspicuous; color — green. Alternate bundle — above stamens. Core lines — meeting; cross section — distinct. Capillary area — distinct; medium size.

*Calyx tube.*—Pubescent; narrowly cone-shaped.

*Stem of funnel.*—Short.

*Depth of tube to shoulder.*—$\frac{1}{2}$ inch.

*Entire depth.*—$\frac{1}{2}$ inch.

*Styles.*—Distinct; pubescent; fused at base.

*Stamens.*—In one distinct whorl; median.

*Auxiliary cavity.*—Wanting.

*Seed cells.* —Abaxile; open. Cell walls — thin; tough, length — $\frac{3}{8}$ inch; breadth — 3/16 inch. Longitudinal section — broadly ovate. Surface — smooth. Cross section — broad.

*Seeds.*—6–8 perfect; not over 2 per cell. Length $\frac{1}{4}$ inch. Breadth — $\frac{1}{8}$ inch. Form — acute. Color — reddish brown.

Use: Dessert, culinary; juice.

Keeping quality: Good; up to $3\frac{1}{2}$ months in ordinary storage.

Resistance to insects and disease: Average resistance to usual insects and diseases to which apple varieties are normally subject.

I claim:

1. The new and distinct variety of Jonathan apple tree substantially as herein shown and described, similar to its parent Jonnee strain of Jonathan apple tree with respect to trunk, branches, leaves, flowers and fruit, but uniquely characterized as to novelty by the significantly earlier coloring and maturing of its fruit.

* * * * *